United States Patent [19]

Grischenko et al.

[11] Patent Number: 4,817,397
[45] Date of Patent: Apr. 4, 1989

[54] DEVICE FOR REFRIGERATION AND FREEZING OF BIOLOGICAL OBJECTS

[76] Inventors: Valentin I. Grischenko, Valery F. Tarasov, Sergei E. Galchenko, Jury V. Kalugin, Jury S. Paraschuk, Nina A. Luchko, Elena N. Chernysh, all of Kharkov, U.S.S.R.

[73] Assignee: Institute Problem Kriobiologii Kriombditsyny Akademii Nauk, Ukrainskoi, U.S.S.R.

[21] Appl. No.: 209,573

[22] Filed: Jun. 21, 1988

[51] Int. Cl.⁴ ............................................. F25B 19/00
[52] U.S. Cl. ..................................... 62/514 R; 62/48; 62/78
[58] Field of Search .......................... 62/48, 78, 514 R

[56] References Cited

U.S. PATENT DOCUMENTS 4,377,077  3/1983  Granlund ............................... 62/78
4,480,682  11/1984  Kaneta et al. ....................... 62/514 R

FOREIGN PATENT DOCUMENTS 989272  7/1981  U.S.S.R. .

OTHER PUBLICATIONS

Big Soviet Encyclopedia, vol. 9, 1973, p. 329.

Primary Examiner—Ronald C. Capossela
Attorney, Agent, or Firm—Ladas & Parry

[57] ABSTRACT

The device comprises a heat-insulated tank containing a refrigerant. The tank accommodates a vessel made of a high heat-conductivity material and filled with a high thermal-conductivity powdered material, wherein a container with biological objects is immersed.

5 Claims, 3 Drawing Sheets

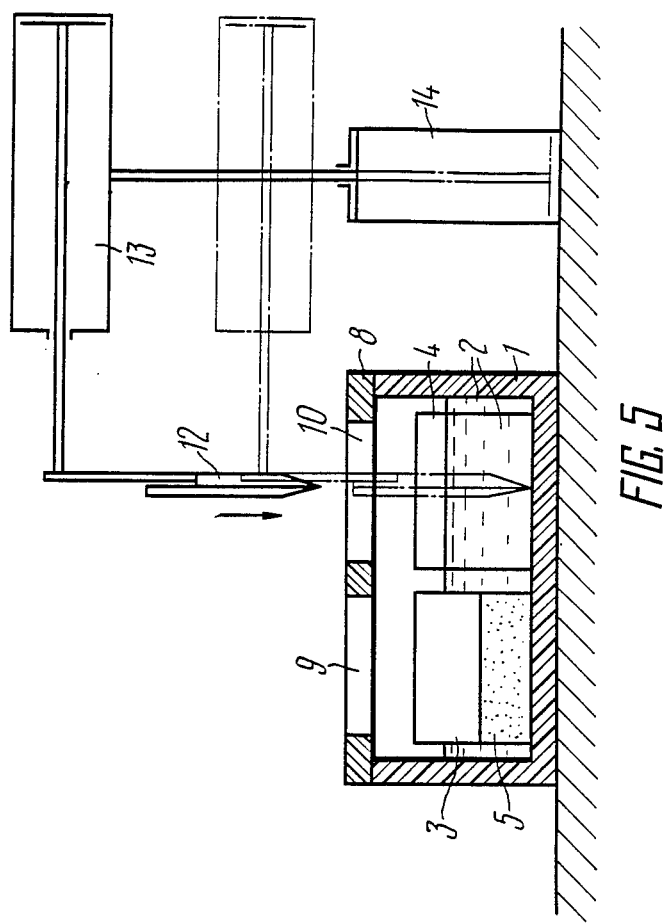

DEVICE FOR REFRIGERATION AND FREEZING OF BIOLOGICAL OBJECTS

FIELD OF THE INVENTION

The present invention relates to cryobiology and cryomedicine and is particularly concerned with a device for refrigeration and freezing of biological objects.

The invention can find most utility when applied for low-temperature preservation of such biological objects as suspensions, liquid or solid tissues and organs which are applicable in clinical practice.

Apart from that the device is applicable for low-temperature refrigeration and freezing of biological objects in farming industry, particularly in animal husbandry.

The invention can also find use for low-temperature preservation of biological objects of any kind whose vitality should be preserved for a prolonged period of time under low temperatures.

The invention can be utilized whenever there is required a considerable curtailing of the refrigeration time of an object, which cannot be attained by any other methods.

Increased requirements of public health service and national economy in high-quality cryopreserved biological material called forth further improvement in the methods of cryopreservation by increasing the efficiency of freezers and simplifying their construction. Since attempts for cryopreservation of biological objects by their fast refrigeration by direct immersion in liquid nitrogen failed to yield satisfactory results, while the operating principle of the now-existing freezers based on development of crystallization processes inflicts considerable damage to the cells being frozen, necessity arose for elaboration of a constructionally simple and practically efficient device for refrigeration and freezing, which would be instrumental in attaining the vitrification effect in biological objects being frozen.

DESCRIPTION OF THE PRIOR ART

Practically all low-temperature freezing methods are based on the principle of programmed refrigeration. To ensure against negative manifestations of the crystallization process, freezing is carried out in a medium of a cryopreservative, while cryoprotectors making part of the cryopreservative composition are not indifferent to biological structures, but are toxic, to one extent or another, and produce a detrimental effect on biomacromolecules, especially when concentration of the cryoprotectors is increased which is concerned with freezing of water and its turning into pure ice. The eutectic concentrations of such cryoprotectors are equal to as high as 60 to 70 percent.

High-accuracy freezing of embryos is carried out with the aid of a device for programmed freezing and thawing of animal embryos (SU, A, No. 989,272), which device comprises a heat-insulated tank for accommodating containers with the embryos therein, holders of the containers, contrivances for stirring an intermediate heat-transfer agent, and a system for control of the freezing process. The tank has a cover, while the device for maintaining the temperature of the intermediate heat-transfer agent is made as a pipe coil located on the inner tank surface so that the coil pitch increases towards the tank bottom, and the holders of the containers are secured in the cover.

It is worth noting that cryoprotection of embryos during their cryopreservation with the aid of the aforementioned device is carried out by the crystallization initiation technique so that development of the crystallization process results in dehydration of the cells being frozen. This makes it possible to avoid intracellular crystallization when carrying the embryos into liquid nitrogen for storing there. Necessity for gradual dehydration of the cells compels one to refrigerate the cells at a slow rate so that the crystallization process develops but too slowly. The biological structures in question are exposed to the effect of extreme factor within such a prolonged period of time as 1.5 to 2 hours said factors being concerned with water freezing and the resulting increase in the concentration of electrolytes, change in the pH value, growth of ice crystals, etc. Under such low-temperature preservation conditions necessity arises for high (1 to 3 M) concentrations of the cryoprotectors, which produce toxic and pseudotoxic effect on the cells under conditions of slow crystallization development and hence prolonged exposure of the cells to the liquid phase.

Apart from that the aforesaid device features but too narrow a range of refrigeration rates, i.e., 0.3 to 1° C./min, which places limitation on the capabilities of the cryopreservation method, thus making one employ largely standard cryopreservatives whose composition interferes with optimization of the now-existing methods. This disadvantage is the more so essential that routine methods for cryopreservation of embryos fail to provide an adequately high and stable rate thereof. This, in turn, tells negatively on the transplanting results in pedigree stock-raising and in public health service using embryos in clinical practice for combatting infertility.

In addition, the device is constructionally sophisticated and incorporates expensive components which are not as a rule equipped with service equipment.

The device needs highly skilled personnel to be attended to, who should be well versed not only in the cryopreservation techniques but also in the skill of setters of such equipment.

It is common knowledge that refrigeration of various materials, e.g., foodstuffs can be carried out by immersing them in liquid nitrogen, freon or nitrogen oxide (cf. Big Soviet Encyclopedia, 3rd edition, Vol. 9, 1973, Sovetskaya Entsiklopedia Publishers, p. 327 (in Russian), and quite a number of devices have been proposed for the purpose.

However, devices adapted for practical implementation of methods for quick refrigeration of biological structures based on direct immersion of containers holding biological material, in liquid refrigerant fail to attain a refrigeration rate exceeding 400 or 500° C./min, which is low enough to avoid the development of the crystallization process even at the aforesaid refrigeration rate.

Therefore recourse should be had in such cases to incorporating high concentrations of a cryoprotector into the cryopreservatives, which amount to 50 or 60 percent, which makes it possible to attain the vitrification process even at the aforesaid refrigeration rate.

However, application of the aforesaid concentrations of cryoprotectors results in heavy damage to biological structures at the stage of addition of cryopreservatives thereto or elimination of the latter after thawing.

Such low refrigeration rates of a biological specimen in the case of its direct immersion in liquid nitrogen are concerned with the fact that a heat-insulating shield is formed round the containers holding the biological specimen, consisting of the vapours of such a refrigerant as, e.g., nitrogen and owing its origin to a temperature difference between the non-cooled container and liquid nitrogen having a temperature of minus 196° C.

Presence of such a shield reduces the refrigeration rate of a biological object to such a level at which crystallization process is developed which, in turn, involves the use of a cryopreservative incorporating high-concentration cryoprotectors for the above process to suppress.

OBJECT AND SUMMARY OF THE INVENTION

It is an object of the present invention to cut down the refrigeration and freezing time for biological objects.

It is another object of the present invention to provide better preservation of biological objects.

It is one more object of the present invention to provide a simpler construction of a device for refrigeration and cryopreservation of biological objects.

It is still one more object of the present invention to provide higher labour productivity.

The foregoing and other objects are accomplished due to the fact that in a device for refrigeration and freezing of biological objects, comprising a heat-insulated tank for a refrigerant and a container for biological objects, according to the invention, the device of the invention is provided with a vessel made of a highly heat-conductive material, said vessel being accommodated in the tank and filled with a high thermal-diffusivity powdered material for the container with the biological objects to immerse in.

The proposed invention makes it possible to rule out formation of a heat-insulating shield of nitrogen vapours round the container with the biological objects which in turn enables one to increase the refrigeration rate of said objects up to a few scores of thousands of degrees per minute depending on the kind of the powdered material, its degree of dispersion and shape of particles thereof.

As a result, the molecules of water have not time enough to get arranged in a crystalline lattice, so that water freezing occurs by its vitrification, which rules out completely or minimizes an adverse effect produced on the biological structures by extreme factors concerned with the development and running of the crystallization process, which adverse effect is manifested in mechanical damage to the biomacromolecules by ice crystals, in the denaturing effect of hyperconcentrated salt solutions and in their osmotic effect, in excess hydration of the biological structures in irreversible injuries to said structures.

In a preferred embodiment of the present invention, a metal is used as the high thermal-diffusivity powdered material.

Advantageously, used as the high thermal-diffusivity powdered material is a metal oxide.

According to one of the alternative embodiments of the present invention a metal alloy is used as the high thermal-diffusivity powdered material.

According to a further embodiment of the present invention a mixture comprising a metal, a metal oxide and a metal alloy taken in various ratios to one another, is used as the high thermal-diffusivity powdered material.

Selection of an appropriate powdered material depends on the time required for vitrification to develop in the biological object being frozen with the use of a cryopreservative of a corresponding formulation.

BRIEF DESCRIPTION OF THE DRAWINGS

In what follows the present invention is illustrated in a detailed description of its specific exemplary embodiments to be read with reference to the accompanying drawings, wherein:

FIG. 5 shows the device of FIG. 1 at the instant when the container with the frozen biological objects is placed in a vessel filled with a refrigerant for being stored there.

BRIEF DESCRIPTION OF THE EMBODIMENTS

Figure 1:
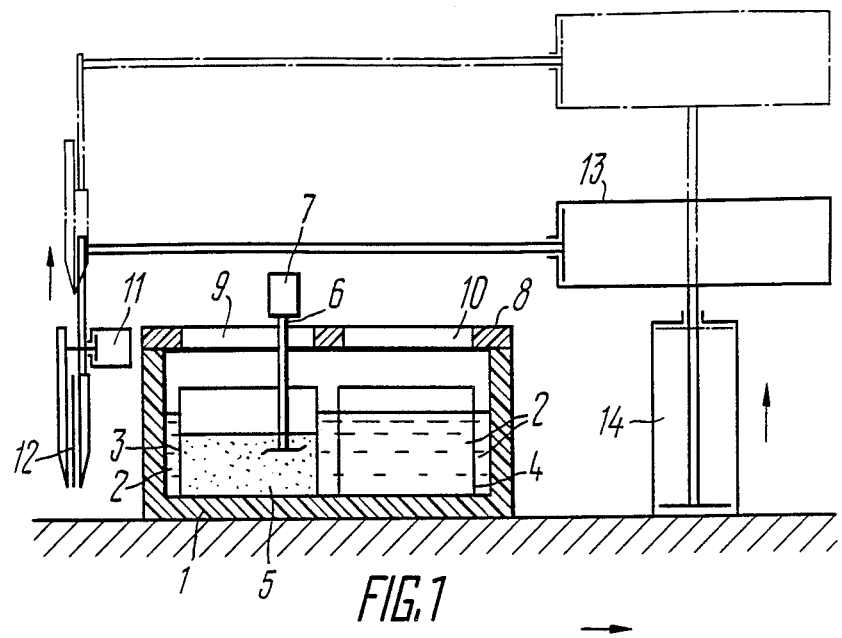
FIG. 1 is a schematic functional diagram of the device, according to the invention, at the instant when the container holding the biological objects is being gripped.

The device of the invention comprises a tank 1 (FIG. 1) made of a heat-insulating material, e.g., foamed plastic, and adapted for being filled with a refrigerant 2. The tank 1 accommodates two vessels 3, 4 made of a high heat-conductivity material, e.g., a metal. The vessel 3 is adapted for filling with a high thermal-diffusivity powdered material 5, while the vessel 4, for filling with the refrigerant 2. A stirrer 6 with an electric drive 7 is installed in the vessel 3. The tank 1 is provided with a cover 8 having two through holes 9, 10 located above the respective vessels 3, 4.

The device is provided with a mechanism 11 for gripping a container 12 holding the biological objects to be frozen, and with drives 13, 14 to impart horizontal and vertical rectilinear motion to the container 12.

The container 12 can be made of, e.g., aluminium foil.

Used as the high thermal-diffusivity material 5 can be a metal, a metal oxide, or a metal alloy taken either individually or in various ratios to one another.

The device of the invention operates as follows.

Figure 2:
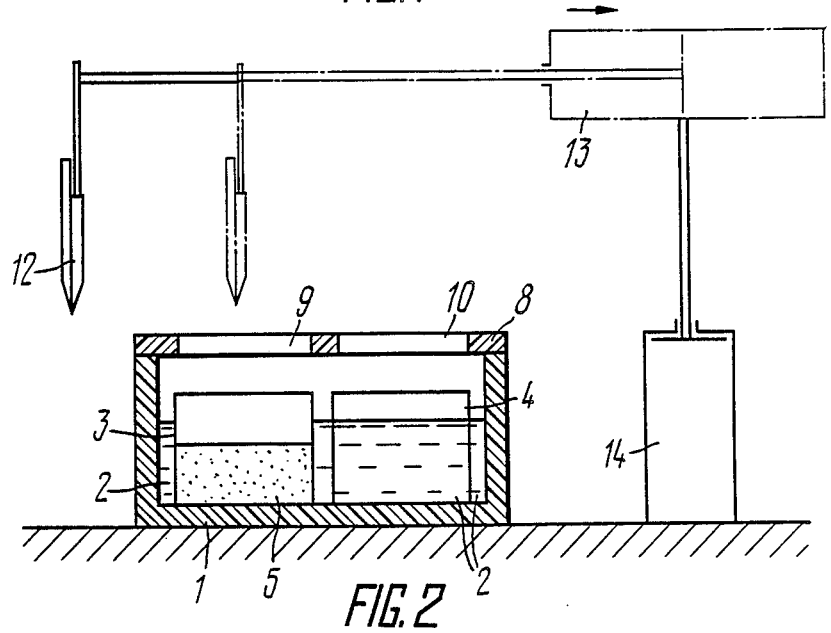
FIG. 2 shows the diagram of the device of FIG. 1 at the instant when the container holding the biological objects is transferred towards the refrigerant tank.
Figure 3:
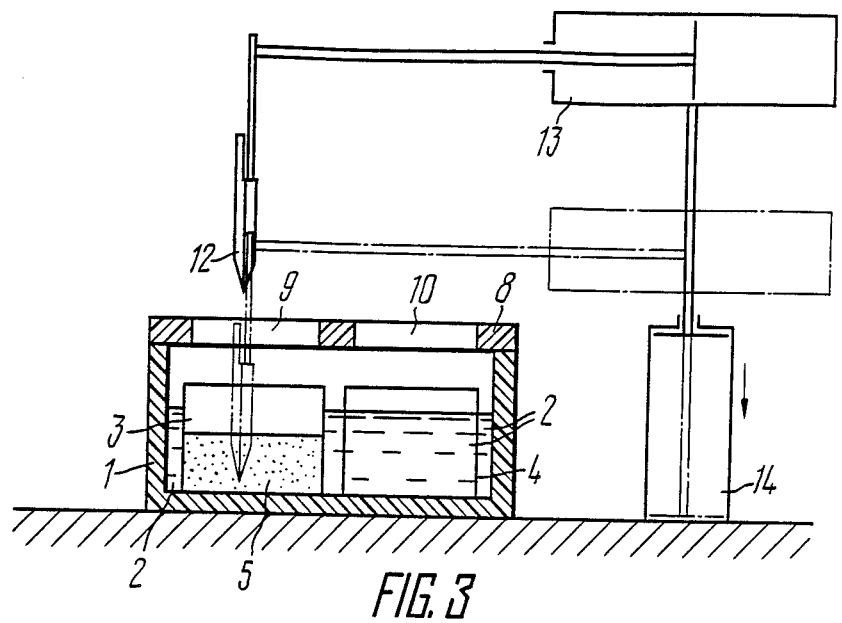
FIG. 3 shows the way the container holding the biological objects is immersed in a vessel filled with a high thermal-diffusivity powdered material.
Figure 4:
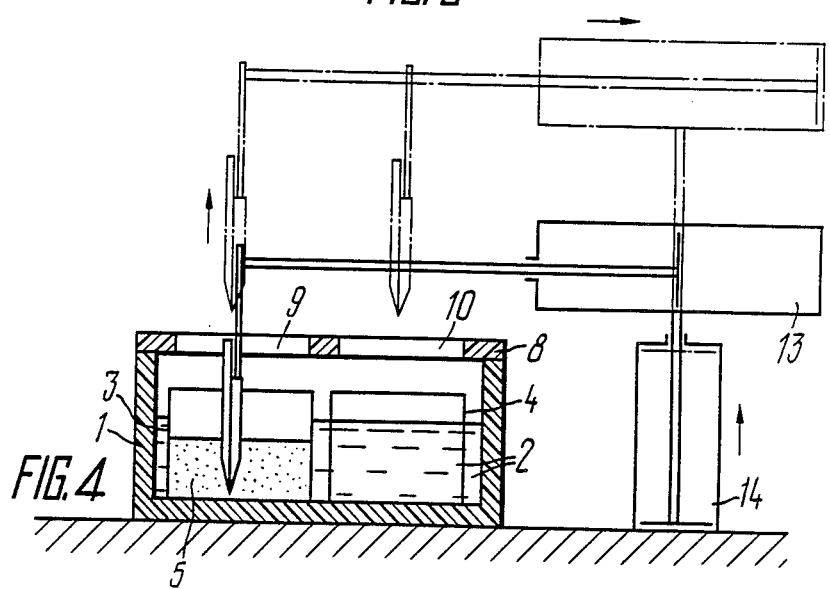
FIG. 4 shows the device of FIG. 1 at the instant when the container holding the biological objects is being withdrawn from the vessel filled with the high thermal-diffusivity powdered material.

Prior to operation the cover 8 is removed and the tank 1 and the vessel 4 are filled with the refrigerant 2, e.g., liquid nitrogen having a temperature of minus 196° C. while the vessel 3 is filled with the high thermal-diffusivity powdered material 5. Then the drive 7 of the stirrer 6 is engaged for balancing the temperature of the material 5 in the vessel 3, whereupon the tank 1 is closed with the cover 8. Once the material 5 has been cooled down to the refrigerant temperature, the container 12 filled with the biological objects is gripped by the mechanism 11 (FIG. 1) and is introduced, using the drives 13, 14, through the holes 9 into the vessel 3 (FIGS. 2, 3) and immersed in the powdered material 5 held in that vessel. In 5 to 10 seconds the container 12 with the frozen biological objects is withdrawn, with the aid of the drives 13, 14, from the tank 1 (FIG. 4) and forwarded to the hole 10, whereupon the container is inserted through said hole into the vessel 4 (FIG. 5) for a short-term storage there (for a few days).

To confirm serviceability of the proposed device there has been carried out refrigeration and freezing of water samples to a temperature of minus 50° C. The container 12 having 0.1 ml capacity and made of foodstuff foil 0.03 mm thick, is filled with water and immersed in the vessel 3 filled with powdered alumina ($Al_2O_3$) cooled down to the temperature of the refrigerant 2. As a result, the temperature of minus 50° C. is attained within 0.95 s. The control biological specimen is placed in the vessel 4 filled with liquid nitrogen, and the time within which a temperature of minus 50° C. is attained equals 1.87 s. The results obtained with the use of other powdered materials are tabulated below.

TABLE

Water solidification time upon immersing the container in high thermal-diffusivity powdered materials and liquid nitrogen

| No. | Powdered material | Water solidification time in container, s |
| --- | --- | --- |
| 1 | Copper | 0.85 |
| 2 | Iron | 0.3 |
| 3 | Zinc | 0.15 |
| 4 | Zinc oxide | 0.75 |
| 5 | Aluminium, coarse grained (100-200µ) | 0.6 |
| 6 | Alumina | 0.95 |
| 7 | Bronze (90% Cu, 10% Sn) | 0.35 |
| 8 | Brass (80% Cu, 20% Sn) | 0.5 |
| 9 | Mixture of $Al_2O_3$ and ZnO (50/50) | 0.9 |
| 10 | Mixture of $Al_2O_3$ (35%), Zn (35%), bronze (30%) | 0.75 |
| 11 | Mixture of $Al_2O_3$ (25%), Zn (50%), bronze (25%) | 0.4 |

TABLE-continued

Water solidification time upon immersing the container in high thermal-diffusivity powdered materials and liquid nitrogen

| No. | Powdered material | Water solidification time in container, s |
| --- | --- | --- |
| 12 | Liquid nitrogen (for comparison) | 1.87 |

The results obtained demonstrate that immersing the vessel 3 filled with the powdered material 5 in the refrigerant, said powdered material serving as a refrigerant for the biological object in the container 12, makes it possible to cut down the solidification time 2 to 15 times, whereby the device can be used in cryobiology and cryomedicine.

What is claimed is:

1. A device for refrigeration and freezing of biological objects, comprising a heat-insulated tank for a refrigerant, a vessel made of a high heat-conductivity material and accommodated in said tank; a high thermal-diffusivity powdered material contained in said vessel; a container for biological objects immersed in said high thermal-diffusivity powdered material held in said vessel.

2. A device as claimed in claim 1, wherein a metal is used as the high thermal-diffusivity powdered material.

3. A device as claimed in claim 1, wherein a metal oxide is used as the high thermal-diffusivity powdered material.

4. A device as claimed in claim 1, wherein a metal alloy is used as the high thermal-diffusivity powdered material.

5. A device as claimed in claim 1, wherein a mixture of a metal, a metal oxide, and a metal alloy taken in various ratios to one another is used as the high thermal-diffusivity powdered material.

* * * * *